United States Patent
Demirtas et al.

(10) Patent No.: US 10,285,651 B2
(45) Date of Patent: May 14, 2019

(54) ON-DEMAND HEART RATE ESTIMATION BASED ON OPTICAL MEASUREMENTS

(71) Applicant: ANALOG DEVICES, INC., Norwood, MA (US)

(72) Inventors: Sefa Demirtas, Malden, MA (US); Jason D. King, Derry, NH (US); Robert Adams, Acton, MA (US); Tony Joseph Akl, Woburn, MA (US); Jeffrey G. Bernstein, Middleton, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 265 days.

(21) Appl. No.: 15/198,438

(22) Filed: Jun. 30, 2016

(65) Prior Publication Data
US 2018/0000424 A1    Jan. 4, 2018

(51) Int. Cl.
*A61B 5/00* (2006.01)
*A61B 5/024* (2006.01)
*A61B 5/11* (2006.01)

(52) U.S. Cl.
CPC ........ *A61B 5/7257* (2013.01); *A61B 5/02416* (2013.01); *A61B 5/1118* (2013.01); *A61B 5/1123* (2013.01); *A61B 5/681* (2013.01); *A61B 5/6802* (2013.01); *A61B 5/7207* (2013.01); *A61B 5/7221* (2013.01)

(58) Field of Classification Search
CPC .. A61B 5/7257; A61B 5/02416; A61B 5/7207
See application file for complete search history.

(56) References Cited

U.S. PATENT DOCUMENTS

| | | | |
|---|---|---|---|
| 6,198,951 B1 * | 3/2001 | Kosuda | A61B 5/02416 600/323 |
| 7,738,949 B2 | 6/2010 | Holland | |
| 8,262,582 B2 | 9/2012 | Kortelainen | |

OTHER PUBLICATIONS

Jayadevappa, B.M. et al., *An Estimation Technique using FFT for Heart Rate Dervied from PPG Signal*, Global Journal of Researches in Engineering: F, Electrical and Electronics Engineering, vol. 15, Issue 7, Version 1.0, Year 2015, 9 pages.

(Continued)

*Primary Examiner* — Michael W Kahelin
(74) *Attorney, Agent, or Firm* — Patent Capital Group

(57) ABSTRACT

Activity monitors and smart watches utilizing optical measurements are becoming widely popular, and users expect to get an increasingly accurate estimate of their heart rate (HR) from these devices. These devices are equipped with a light source and an optical sensor which enable estimation of HR using a technique called photoplethysmography (PPG). One of the main challenges of HR estimation using PPG is the coupling of motion into the optical PPG signal when the user is moving randomly or exercising. The present disclosure describes a computationally feasible and fast HR estimation algorithm to be executed at instances of little or no motion. Resulting HR readings may be useful on their own, or be provided to systems that monitor HR continuously to prevent the problem of such systems being locked on an incorrect HR for long periods of time. Implementing techniques described herein leads to more accurate HR measurements.

20 Claims, 6 Drawing Sheets

(56) References Cited

OTHER PUBLICATIONS

J. Guyomard et al., *Heart Rate Measurement through PPG, Heartbeat measurement in a wireless headset*, Delft University of Technology, Apr. 20, 2015-Jul. 3, 2015, 56 pages.

Toshiyo Tamura et al., *Wearable Photoplethysmographic Sensors—Past and Present*, Electronics, 2014, 3, 282-302; DOI: 10.3390/electronics3020282, Open Access Electronics, ISSN 2079-9292, www.mdpi.com/journal/electronics, 21 pages.

Zhi Lin et al., *Heart Rate Estimation Using Wrist-acquired Photoplethysmography Under Difference Types of Daily Life Motion Artifact*, 2015 IEEE International Conference on Communications (ICC), 489-494, DOI: 10.1109/ICC.2015.7248369, Jun. 8-12, 2015, 6 pages.

*Photoplethysmography (PPG) System*, Geert Langereis, Version 2, Feb. 2010, 22 pages.

International Search Report and Written Opinion issued in International Patent Application Serial No. PCT/US2017/039878 dated Oct. 3, 2017, 10 pages.

\* cited by examiner

ON-DEMAND HEART RATE ESTIMATION BASED ON OPTICAL MEASUREMENTS

TECHNICAL FIELD OF THE DISCLOSURE

The present invention relates to the field of digital signal processing, in particular to digital signal processing for estimating heart rate based on optical measurements.

BACKGROUND

Modern electronics are ubiquitous in healthcare. For example, monitoring devices often include electronic components and algorithms to sense, measure, and monitor living beings. Monitoring equipment can measure vital signs such as respiration rate, oxygen level in the blood, heart rate, and so on. Not only are monitoring devices used in the clinical setting, monitoring devices are also used often in sports equipment and consumer electronics.

One important measurement performed by many of the monitoring equipment is heart rate, typically measured in beats per minute (BPM). Athletes may use heart rate monitors to get immediate feedback on a workout, while health care professionals may use heart rate monitors to monitor the health of a patient. Many solutions for measuring heart rate are available on the market today. For instance, electronic heart rate monitors can be found in the form of chest straps and watches. Chest straps are often quite accurate, but they may be quite bulky and wearing them is not always comfortable or desirable. More compact electronic heart rate monitors such as e.g. watches are often not very accurate due to a high amount of noise present in the signals provided by the sensors of these monitors. The noise is often caused by the fact that the user is moving and also by the lack of secure contact between the monitor and the user. This noisy environment often leads to an irregular, inaccurate or even missing readout of the heart rate.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Figure 1:
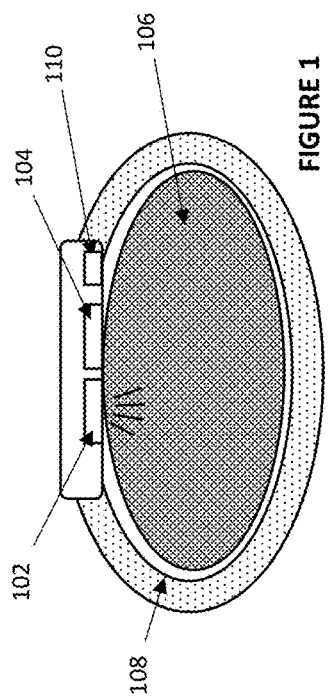
FIG. 1 shows an illustrative heart rate measuring apparatus and a portion of a living being adjacent to the heart rate monitor, according to some embodiments of the disclosure.

Activity monitors and smart watches utilizing optical measurements are becoming widely popular, and users expect to get an increasingly accurate estimate of their heart rate (HR) from these devices rather than wear uncomfortable but more accurate chest straps. These devices are equipped with a light source, e.g. a light emitting diode (LED), and an optical sensor which enable estimation of HR by optical measurements using a technique called photoplethysmography (PPG). The LED illuminates the back of the wrist and the backscattered light is recorded by the optical sensor. The HR can then be estimated by measuring the period of the fluctuations of the optical signal, caused by the periodic change in the amount of blood in the wrist and the resulting change in light absorption with each beat of the heart.

One of the main challenges of HR estimation using PPG is the coupling of motion into the optical signal (PPG signal) when the user is moving randomly or exercising, resulting in undesired swings and distortion in the PPG signal on the order of fifty to a hundred times the actual footprint of the heartbeat, i.e. a noisy PPG signal. Noisy PPG data makes it difficult for the systems to output a consistently accurate heart rate reading. Using known methods for processing accelerometer readings that measure movement to filter out some of this noise may help to a certain extent, but not always. The present disclosure describes a computationally feasible and fast HR estimation method to be executed at instances of little or no motion and high PPG signal quality in order to obtain a very accurate estimate of user's HR. Instances of little or no motion could e.g. take place when a user is cooperating with the measurement system and is trying to be as still as possible, i.e. the measurement system may be operating "on-demand" by the user and the user is cooperating. The method includes performing a set of confidence/quality checks on the acquired PPG and accelerometer data to assess whether the PPG data may be assumed to be of sufficiently high quality (i.e. has a limited amount of noise) to carry out HR estimation from that data, computing HR estimates from such PPG data using at least two different algorithms (possibly applied to PPG data of different but overlapping time periods), and declaring a final result for the HR based on these multiple HR estimates. Resulting HR readings may be useful as such, e.g. if a user wants to measure his/her HR before or after exercise, and/or be provided to systems that track HR (i.e. measure the HR continuously, e.g. throughout the duration of exercise), to e.g. prevent the problem of such systems being locked on an incorrect HR for long periods of time or provide a reference when the signal quality is high. Implementing the HR estimation techniques described herein may lead to more accurate HR measurements.

Understanding Issues of Noisy Environment of Heart Rate Monitors

Heart rate monitors are often in direct contact with the skin of a living being. The monitors passively measure or track heart rate by sensing one or more aspects of the skin adjacent to the heart rate monitor. Due to the passive nature of such measurements, the sensor data can be affected by many sources of noise which severely affects the ability of the heart rate monitor to determine an accurate heartbeat.

These sources of noise can include external interference to the sensor, internal noise of the sensor and/or heart rate monitor, motion causing disruptions in the sensor's capability in measuring the aspects of the skin, etc. Furthermore, heart rate monitors are affected by variability in the skin of different living beings and the variability of the skin and environment during the use of the heart rate monitor. All these different sources and issues have adverse impact on the heart rate monitor's ability to extract an accurate heart rate.

FIG. 1 shows an illustrative heart rate measuring apparatus and a portion of a living being adjacent to the heart rate monitor, according to some embodiments of the disclosure. In particular, the FIGURE shows a cross section to illustrate the monitoring apparatus's spatial relationship with the portion of the living being. In this exemplary heart rate monitoring setup, a PPG method is used, where the heart rate is measured passively or indirectly based on changes in light absorption in the skin as blood is pushed through the arteries. Changes in blood volume as blood is pumped through the arteries results in a variation in the amount of received light, which is translated into electrical pulses by an optical sensor. The pulses in the signal can then be used in extracting a heart rate.

Heart rate measuring apparatus described herein are not limited to the particular example shown in FIG. 1. Although the disclosure does not describe other types of heart rate monitors in detail, one skilled in the art would appreciate that these challenges are also applicable in other types of heart rate monitors or other types of devices providing heart rate monitoring functions, or even devices utilizing other types of sensing mechanism. Furthermore, the continued process of measuring, following, extracting, determining, or sensing the heart rate over time is referred to as "tracking a heart rate", within the context of the disclosure.

Specifically, FIG. 1 illustrates an exemplary heart rate measuring apparatus having a light source 102 and an optical sensor 104. The light source can emit light within a range of wavelengths suitable for the application. In some embodiments, the light source 102 and the optical sensor 104 can be provided separately, or a light source 102 can be biased to function as an optical sensor 104. For instance, a red LED can be used as a red light source and a red optical detector. In some embodiments, both the light source 102 and optical sensor 104 can be provided nearby each other in a housing or member of the heart rate measuring apparatus or in any suitable configuration where the optical sensor 104 can measure absorption of light (as generated by the light source 102) by the part 106 of the living being. The light source shines a light onto a part 106 of a living being 106 and the optical sensor 104 measures light incident onto the optical sensor 104, which can include light being reflected from the part 106 as well as ambient light. Various parts of the living being can be used as part 106, e.g., a finger, an arm, a forehead, an ear, chest, a leg, a toe, etc., as long as changes in the volume of blood can be measured relatively easily. The part 106 can, in some cases, be internal to the body of the living being.

Generally speaking, if the heart rate measuring apparatus can be affixed to the part 106 of the living being securely and maintain relatively stable contact with the part 106 during use, the input signal provided by the optical sensor could exhibit very little noise and the heart rate could be extracted relatively easily. However, in many scenarios, the heart rate measuring apparatus is not securely affixed to the part 106 (even with the use of part 108 involving a band, a strap, adhesive, or other suitable attachments), or having the apparatus securely adhered or attached to the part 106 is not desirable or comfortable for the living being. Even when sensor is securely connected, motion can affect signal quality greatly because of blood rushing in and out of the veins during motion in large amounts. In these scenarios, the signal provided by the optical sensor 104 may be affected by artifacts caused by motion of the heart rate measuring apparatus, noise from ambient light, or by some other noise source. As a result, correctly detecting the heart rate in these non-ideal scenarios, i.e., in a noisy environment, can be challenging. Attempting to detect the heart rate based on a noisy signal can result in irregular or erroneous heart rate readings. To make things even worse, even determining whether the readings output by the heart rate measuring apparatus are trustworthy may be difficult (i.e. the confidence level in the resulting readings may be inadequately low).

To address this issue, a heart rate measuring apparatus can include an accelerometer 110 to measure the motion of the apparatus to assess whether the input PPG signal is likely to be too degraded by motion artifacts to be relied upon for heart rate determination. Some use scenarios for such an accelerometer are based on recognition that, when a sensor, or multiple sensors, configured to generate an input signal from which the heart rate is to be determined (such sensor or a plurality of sensors referred to in the following as a "heart rate sensor") are moving (e.g. because a living being wearing such heart rate measuring apparatus is running), their measurements are affected by the movement in a predictable manner. Therefore, if the pattern of motion is known, then it may be possible to identify contributions to the input signal that are attributable to the motion of the heart rate sensor (i.e., motion-related artifact in the input signal) and filter those contributions out. Provided that a heart rate sensor is in relatively close proximity to an accelerometer so that both the accelerometer and the heart rate sensor experience the same motion, accelerometer measurements taken at the same time as the measurements by the heart rate sensor may be considered to accurately represent motion of the heart rate sensor when the input signal was acquired. In turn, accelerometer data related to the motion of the heart rate sensor may be used in improving HR estimation, e.g. by reducing the amount of noise in the input signal generated by the sensor by identifying motion-related artifacts in the input signal, by applying various noise filtering techniques, or by causing the apparatus to discard measured data or freeze the heart rate readout when the accelerometer 110 senses too much motion.

Using accelerometer data in heart rate estimation can be helpful to a certain extent but even then readings can be erroneous or getting to the heart rate that has a high confidence level can take unacceptably long amount of time. Therefore, further improvements in estimating heart rate quicker, more accurately, and/or with higher confidence are always desirable.

Overview of an Improved HR Estimation Mechanism

Embodiments of the present disclosure provide an improved HR estimation approach when a living being is relatively motionless. Some example use cases include a living being cooperating with the HR measurement by trying to be as still as possible, e.g. at the beginning or the end of exercise, during spontaneous inquiry of HR, etc. Other example use cases may include a living being in a relatively motionless state for other reasons, e.g. a living being is unconscious or too weak to move. When a living being is still, the PPG data is of higher quality because the amount of motion-related artifacts is reduced, enabling fast estimation of the heart rate because it is not necessary to perform complicated motion rejection or filtering algorithms or because the complexity of such algorithms can be greatly simplified. However, heart rate estimation still requires high confidence in the final estimate. Heart rate estimation approaches described herein are based on recognition that using a carefully selected set of quality metrics involving accelerometer data and PPG data and employing at least two different algorithms for heart rate estimation to compare the results against one another would provide the necessary high confidence in accurately determining the heart rate relatively fast, e.g. an estimate with 2-5 beats per minute (bpm) accuracy obtained in 5 to 8 seconds.

An Exemplary Improved Heart Rate Measuring Apparatus and Method

Figure 2:
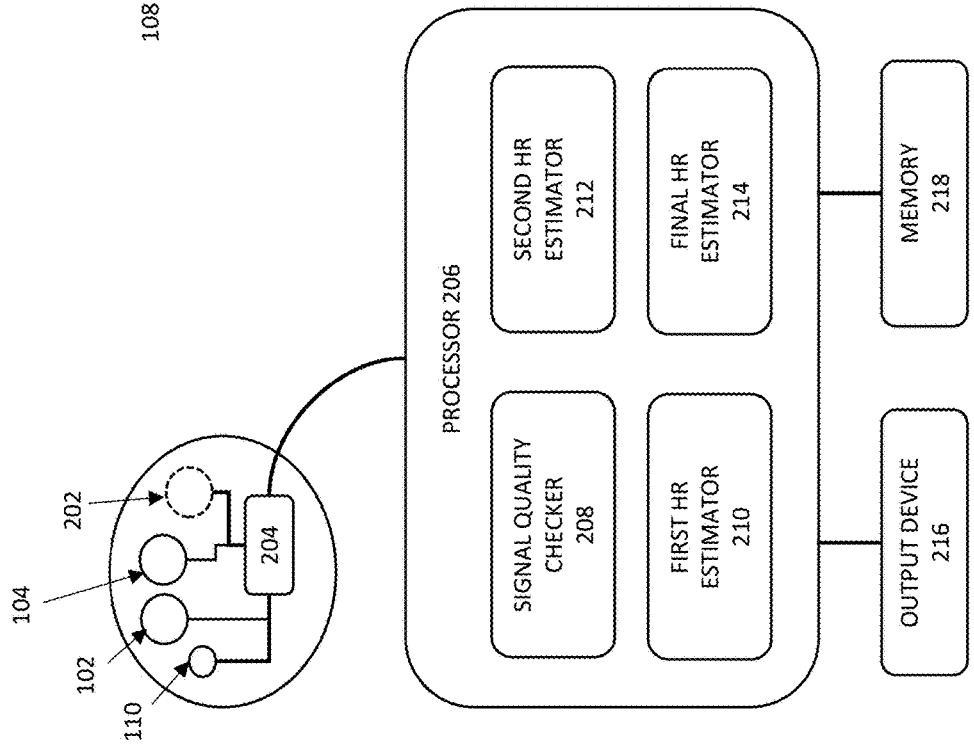
FIG. 2 illustrate a system view of a heart rate measuring apparatus, according to some embodiments of the disclosure.

FIG. 2 illustrates a system view of a heart rate measuring apparatus, according to some embodiments of the disclosure. The system provides an arrangement of parts for implementing or enabling a method for determining a heart rate from a heartbeat signal present in one or more PPG input signals provided by one or more sensors (heartbeat sensors) in an environment that may be noisy. As used herein, in context of a "heartbeat sensor", the term "heartbeat" is merely used to differentiate sensors generating PPG data from other sensors, such as e.g. accelerometers. The term "heartbeat signal" refers to a contribution of a heartbeat source to the PPG signal generated by the heartbeat sensor. In other words, the "heartbeat signal" refers to a signal indicative of (i.e. being representative of) the heartbeat of the living being that is being evaluated.

Similar to FIG. 1, the apparatus of FIG. 2 may include a light source 102 and an optical sensor 104. The light source can be a light emitting diode (LED), or any suitable component for emitting light. The light emitted by the light source 102 for measuring heart rate (e.g., blood volume) can be any suitable wavelength depending on the application. The apparatus can include a plurality of light sources emitting a range of wavelengths of light. The optical sensor 104 may be the same device as the light source 102, or the optical sensor 104 may be provided near the light source 102 to measure light near the optical sensor 104, e.g., to measure absorption of light emitted by the light source 102 in the skin to implement PPG. In addition, the apparatus includes an accelerometer 110 to measure acceleration/motion of the overall apparatus based on the principles described above with reference to FIG. 1. Furthermore, the apparatus may, optionally, include other sensors 202 or other types of sensors, which can provide information to assist in filtering of the input signal and/or heart rate measurement/tracking. An analog front end module 204, which could include e.g. one or more integrated circuits, may be provided to drive the light source 102 and provide an analog front end to receive signals provided by the optical sensor 104, accelerometer 110, and other sensors 202. In some embodiments, the analog front end 204 can convert (if desired) analog input signals to data samples of the analog input signal. The analog front end can communicate with a processor 206 to provide the data samples, which the processor 206 would process to determine the heart rate.

In various embodiments, the processor 206 can include one or more processing units, microprocessors, application specific parts or modules, electronic circuits, and/or programmable logic gates specially arranged for processing the data samples of the input signal to determine the heart rate according to various methods described herein. The processor 206 can be a digital signal processor provided with application specific components to determine the heart rate, and/or the processor can execute special instructions (stored on non-transitory computer readable-medium) for carrying out various methods of determining heart rate as described herein. In carrying out determination of the heart rate using the methods described herein, the processor 206 may make use of a memory 218, e.g. the memory 218 may store processor-executable instructions for carrying out the methods described herein or/and may store data that the processor may use in determining the heart rate, such as e.g. results of intermediate computations.

Figure 3:
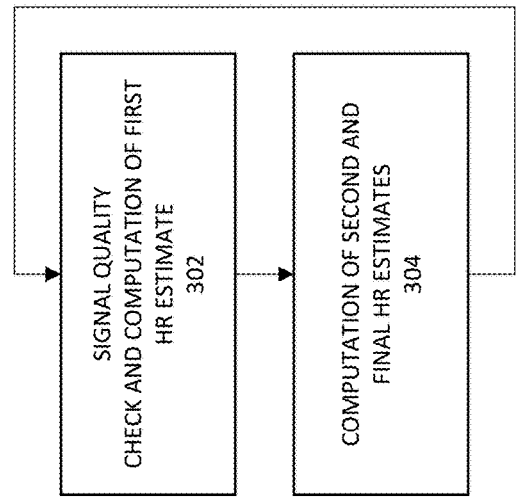
FIG. 3 illustrates an exemplary flow diagram of a method for determining a heart rate from a PPG signal, according to some embodiments of the disclosure.

FIG. 3 illustrates an exemplary flow diagram of one method 300, e.g. implemented by the processor 206 shown in FIG. 2, for determining heart rate from a heartbeat signal present in one or more input signals provided by one or more sensors, e.g. sensors 104, according to some embodiments of the disclosure. At a high level, the method 300 may include signal quality check and computation of a first heart rate estimate component 302 and computation of a second and a final heart rate estimate 304 (dependent on the signal quality check and heart rate estimation in 302). From the final heart rate estimate 304 the method 300 can continue back to the signal quality check and first heart rate estimate 302 to process other data samples in the stream of data samples of the input PPG signal.

Referring to both FIG. 2 and FIG. 3, in some embodiments, the parts of processor 206 may include one or more of the following: a signal quality checker 208, a first heart rate estimator 210, a second heart rate estimator 212, and a final heart rate estimator 214, e.g. to implement the method shown in FIG. 3.

The signal checker 208 may be configured to implement functions related to checking quality of the incoming PPG signal by using accelerometer data to evaluate presence and/or the amount of motion of the heartbeat sensor generating the PPG signal. In some embodiments, the signal quality checker 208 may correspond to the signal quality check and computation of first heart rate estimate 302 of the method shown in FIG. 3. However, the signal quality checker 208 may also be configured to perform additional signal quality checks previous to, subsequent to, or performed at least partially in parallel with computing the first heart rate estimate.

The first HR estimator 210 may be configured to implement functions related to processing data samples of the input signal based on the decision(s) in the signal checker 208 to provide an estimate of the HR using a first method. Such a first method may involve computation of an auto-correlation function (AF) or a Square Difference Function (SDF) which yields results similar to those of the autocorrelation function. In some implementations, the results provided by an SDF may be viewed to be complementary to those provided by an autocorrelation function. The first HR estimator 210 may correspond to the signal quality check and computation of first HR estimate 302 of the method shown in FIG. 3.

The second HR estimator 212 may be configured to implement functions related to processing data samples of the input signal, possibly based on the decision(s) in the signal checker 208, to provide an estimate of the HR using a second method. Such a second method may involve computation of a frequency-domain representation, e.g. a Discrete Fourier Transform (DFT), of the data samples of the PPG signal that passed certain quality checks.

The final HR estimator 214 may be configured to compare the outcomes of the first and second HR estimations and provide a final estimate of the HR. The second HR estimator 212 and the final HR estimator 214 may correspond to the computation of second and final HR estimates 304 of the method shown in FIG. 3.

In various embodiments, the processor 206 may also implement other components not shown in FIG. 2. For example, the processor 206 may include a signal conditioner configured to prepare the data samples of the PPG and/or accelerometer signals for processing by the signal quality checker 208, the first HR estimator 210, the second HR estimator 212, and/or the final HR estimator 214. For instance, such a signal conditioner could be configured to filter data samples of the input signal(s) a certain way (or apply a filter on the data samples), apply a mask to the data samples, attenuate certain data samples, modify the values of certain data samples, and/or select certain data samples from a particular sensor for further processing. The signal conditioning process can depend on the output(s) of the signal quality checker 208.

In another example, the processor 206 may include a decimator configured to decimate the data samples of the PPG and/or accelerometer signals, e.g. in order to reduce the number of data samples to process and hence increase computational efficiency, or/and in order to increase the frequency resolution for locating the DFT peak more accurately. In yet another example, the processor 206 may further include a tracker configured to implement functions related to tracking the heart rate, i.e. continuous measurement of the heart rate, e.g. based on the output from the final HR estimator 214.

The output of the final HR estimator 214 (e.g. determined heart rate in beats per minute), as well as the intermediate outputs of the signal quality checker 210, the first HR estimator 210 and the second HR estimator 212, can be output, e.g. provided to a user, via an output device 216. The output device 216 which could include any suitable output device such as e.g., a speaker, a display, a haptic output device, etc. Information provided at the output device 216 could e.g. assist the user or/and healthcare professionals in assessing whether the user has any underlying conditions relating to heart and arterial health.

Components of the processor 206, such as e.g. the signal quality checker 208, the first HR estimator 210, the second HR estimator 212, and the final HR estimator 214, can include means for performing their corresponding functions. Data and/or instructions for performing the functions can be stored and maintained in the memory 218, which may be or comprise a non-transitory computer-readable storage medium.

The apparatus shown in FIG. 2 is merely an example of a heart rate apparatus, and it is envisioned that other suitable arrangements can be provided to implement the improved methods for HR estimation as described herein.

Since embodiments of the present disclosure are based on computing AF and/or SDF and DFTs, basics of these techniques in context of HR estimation are now described.

Basics of AF and SDF

As is well-known, autocorrelation, also known as serial correlation or cross-autocorrelation, refers to cross-correlation of a signal with itself at different points in time (that is what the cross stands for). In general, a computed autocorrelation is indicative of the similarity between observations as a function of the time lag between them and is often used as a mathematical tool for finding repeating patterns, such as the presence of a periodic signal obscured by noise, or identifying the missing fundamental frequency in a signal implied by its harmonic frequencies. AF is often used in signal processing for analyzing functions or series of values, such as time domain signals.

On the other hand, Square Difference unction (SDF) refers to a function that is computed as the sum of squares of differences between a data array and its time delayed or time advanced version. Similar to AF, SDF is also indicative of repeating patterns in data samples. However, SDF also provides a complementary view to AF because the local minima of the SDF imply similarity of observations as a function of time lag whereas an analogous implication is made by the local maxima of the AF.

Since heartbeat is typically reasonably periodic, presence of a heartbeat signal within an acquired PPG signal may be evaluated using AF as well as SDF. In some embodiments, both AF and SDF methods may be employed.

Basics of DFT

Behavior of signals can be analyzed in the time domain (e.g., how the signal amplitude varies over time) as well as the frequency domain (i.e., the different frequency components that make up the signal), where the Fourier Transform (FT) mathematically relates these two domains. In addition, a signal can be analyzed as a continuous waveform or, in digital-signal processing (DSP) applications, as a large set of time-domain points. Fast Fourier Transforms (FFTs) refer to algorithms for calculating Discrete Fourier transforms (DFTs), as well as their inverses (IDFTs), of signals represented in digital form. Because of the ubiquitous use of Fourier transforms across signal-processing applications, efforts have been made to improve its execution computationally—hence the many FFT approaches, such as e.g. decimation in time, decimation in frequency, radix-2, radix-4, mixed radix, etc.

Results of applying FFT algorithms are typically arranged in one-dimensional or a multi-dimensional array or tensor, indexed appropriately, where one of the dimensions indexes frequencies or frequency ranges. Each element of a computed FFT presented as an array of values is typically referred to as a "frequency bin" or simply a "bin," the term "bin" being indicative of the fact that such an array may be considered as comprising a plurality of bins into which the energy of the acquired signal(s) is distributed. In various embodiments, the bins may contain either complex values or real values. For example, the real values could be presented in terms of positive real quantities X(f) of the complex values, the quantities X representing magnitudes of various frequency components f of the acquired signal, presented e.g. as an actual magnitude, a squared magnitude, or as a compressive transformation of a magnitude, such as a square root or a logarithm. In other examples, the real values could be presented in terms of either positive or negative real quantities X(f) of the complex values, the quantities X representing phases of various frequency components f of the acquired signal.

Frequency bins come into play in context of FFT algorithms employed by various receivers in that separation of a particular signal of interest from the total signal acquired by a receiver, in this context separation of the heartbeat signal, may be achieved by identifying which bin(s) correspond to the signal of interest and/or by identifying which bin(s) may be active. To that end, bins are evaluated to determine whether they contain values that satisfy one or more predefined criteria. For example one criterion could include comparing a value of a bin with a certain threshold value to determine whether the bin may be classified as containing a "peak" indicating that relatively large amount of energy of the acquired signal is concentrated in that bin. Various algorithms may be carried out in order to determine where to set the level threshold to indicate presence or absence of a peak in each bin, all of which algorithms are within the scope of the present disclosure.

Exemplary Implementations of Improved HR Estimation Mechanisms

Embodiments of the present invention are applicable both to determining the HR from an input signal (e.g. PPG signal) as such, as well as to assisting in tracking of the HR by providing the determined HR to particular tracking algorithms being implemented to act as a confidence check.

Figure 4:
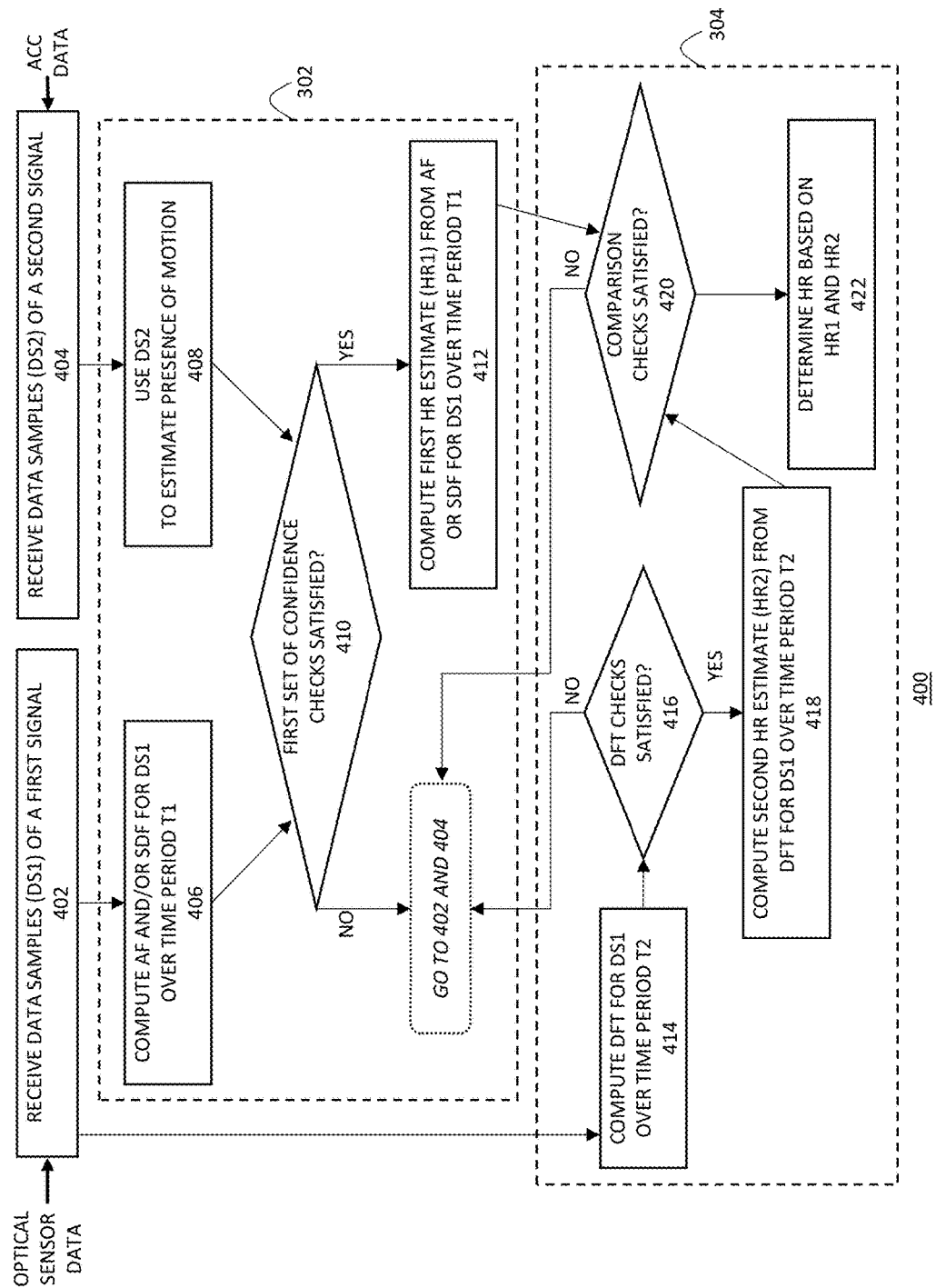
FIG. 4 illustrates additional details of a method for determining a heart rate from a PPG signal, according to some embodiments of the disclosure.

FIG. 4 illustrates an exemplary flow diagram of a more detailed method 400 for determining a heart rate from a PPG signal, according to some embodiments of the disclosure.

The method 400 may begin with receiving data samples of a first signal, abbreviated in FIG. 4 as "DS1" (i.e., an input signal such as e.g. a PPG signal) (step 402). The first signal can be generated by a heartbeat sensor such as e.g. an optical sensor, and typically, the first signal is processed by an analog front end, e.g. the analog front end 204, to produce (digital) data samples of the first signal. In the following, the terms "first signal" and "PPG signal" may be used interchangeably.

The first signal typically has a variety of contributions from various signal sources, some of them being undesirable noise contributions. The first signal may also have a contribution from a heartbeat of a living being and it is from this heartbeat signal present in the first signal that the heart rate may be estimated.

The method 400 also includes receiving data samples of a second signal (step 404). The second signal can be generated by a device capable of detecting and quantifying motion of the heartbeat sensor(s), an accelerometer being one example of such a device. In order to quantify motion in all three orthogonal directions, the second signal preferably comprises three channels, one channel being for each accelerometer axis, detecting motion in that direction. Preferably, the second signal is acquired at the same time as the first signal and the two signals may be processed synchronously, thus providing the closest overlap between the motion of the heartbeat sensor(s) as inferred from the data acquired by the motion sensor and the data representative of the heartbeat acquired by the heartbeat sensors. Similar to the first signal, in some cases, the second signal may be processed by an analog front end to produce (digital) data samples of the second signal.

The data samples of the first and second signals are received by a processor for HR estimation, e.g. the processor 206. Although not specifically shown in FIG. 4, in some embodiments, the first signal may be filtered, e.g. using a band-pass-filter within a reasonable range of heart rates, possibly with a certain margin to account e.g. for imperfect filter roll-off characteristics, e.g. with the range being between 0.4 Hz to 5 Hz, corresponding to 24 bpm to 300 bpm heart rates, respectively. Additionally or alternatively, although also not specifically shown in FIG. 4, in some embodiments, the second signal may also be filtered, e.g. also using a band-pass-filter within a reasonable range of heart rates. The bands of frequencies filtered by the filters applied to the first and second signals may be the same or different. For example, the second signal may be filtered with a somewhat larger passband, e.g. 0.4 Hz to 10 Hz. In other embodiments, low-pass filters may be used instead.

The processor 206 may then process the data samples of the first signal to compute an autocorrelation and/or an SDF of data samples of the PPG signal within a certain time period T1 (step 406), referred to herein as a "first time period". For illustrative purposes, descriptions provided below refer to the processor 206 using autocorrelation function to evaluate heart rate. However, these descriptions can easily be extended to embodiments that would use an SDF or a combination of AF and SDF, all of these embodiments being, therefore, within the scope of the present disclosure. In still further embodiments, step 406 may include the processor 206 processing the data samples of the first signal in any other manner that would allow determination, in step 412, of the first HR estimate from the results of such processing. For example, any of the known HR estimation techniques may be used in that step.

In some embodiments, the processor 206 may be configured to continuously compute autocorrelation for the last T1-period worth of data samples of the incoming PPG signal.

Assuming a sampling rate of the first signal being e.g. Fds1 Hz and T1 being measured in seconds, in step 406 the processor 206 would compute an autocorrelation on Fds1*T1 data samples of the PPG signal. For example, for a sampling rate equal to 100 Hz and an autocorrelation time period equal to 4 seconds, in step 406 the processor 206 may perform an autocorrelation on 400 samples.

The processor 206 also processes the data samples of the second signal from the motion sensors to evaluate presence of motion (step 408), which may be performed at least partially simultaneously with, before, or after the processing of the data samples of the first signal in step 406. As previously described herein, the second signal is assumed to be representative of the motion of the heartbeat sensor(s) acquiring the first signal. Therefore, evaluating presence of motion from the second signal allows the processor 206 to evaluate motion of the heartbeat sensor during the time the first signal was acquired, in particular during the first time period T1 for which the autocorrelation is computed.

In some embodiments, the processor 206 may employ various known algorithms for evaluating presence of motion, with various threshold as to what is considered "motion", when performing step 408, all of which algorithms being within the scope of the present disclosure. In some embodiments, the processor 206 may evaluate motion in step 408 as follows.

The processor 206 may compute and sum the absolute values of each of the accelerometer channel signals and then filter the sequence of sums by a low-pass filter to extract an envelope-like signal that may be referred to as "activity". In embodiments where the second signal from the accelerometer channels may have been scaled previously (not explicitly shown in the drawings), this activity signal may be compared to a specific threshold value, e.g. a threshold value of 0.10, to determine whether there was significant motion during a particular time period. In some embodiments, in order to avoid the filter latency and quickly react to a start of a motion period, a parameter (denoted "b") that determines the location of the pole of a first order low-pass filter may be chosen as a function of a sampling frequency (denoted "$f_s$") for the data samples of the second signal. For example, for a low-pass filter having a filter transfer function defined as $$\frac{b}{1-(1-b)z^{-1}}$$

the parameter b may be selected as $$b = 1 - e^{-0.2231 \frac{100}{f_s}}$$

so that the obtained activity signal crosses a given threshold approximately the same amount of time after the onset of motion regardless of the sampling rate $f_s$.

The processor 206 may then evaluate the outcomes of steps 406 and/or 408 to determine whether a predefined first set of signal quality checks is satisfied (step 410). The first set of quality checks are designed to provide a first evaluation as to the quality/usability of the PPG signal acquired in the time period T1. The processor 206 determining that this set of quality checks is not satisfied means that the PPG signal acquired in the time period T1 may not be of sufficiently high quality to be able to have high confidence in HR estimation based on it. In such a case, the method proceeds back to steps 402 and 404 where more data samples of the first and second signals are received and processed. If, however, the processor 206 determines in step 410 that the first set of quality checks is satisfied, which indicates that the PPG signal in the time period T1 was of sufficiently high quality to yield reliable HR estimation, then the method 400 may proceed to step 412, where the processor 206 computes a first HR estimate from the autocorrelation that was computed in step 406.

In the embodiments where the SDF was computed in step 406 instead of the autocorrelation, then step 412 would involve the processor computing a first HR estimate from the SDF that was computed in step 406.

In some embodiments, step 406 may involve the processor 206 computing both the AF and the SDF. In such embodiments, the processor 206 may be configured to compute the first HR estimate in step 412 based on both the AF and the SDF computed for the data samples over the first time period. For example, the processor 206 may be configured to compute a function which may be referred to as a "combination function" because it combines the results of AF and SDF. One way to compute such a function could be to compute each value of the function as 1−SDF/(SDF+ 2*AF), in which formula SDF and AF represent corresponding values of the SDF and AF (i.e. values for the same time lag). Such a combined function may be evaluated to not only determine the first HR estimate from it, but could also be evaluated as a confidence metric, similar to how the autocorrelation result may be used in a confidence/quality check, as described herein.

Various embodiments envision different quality checks that may be performed by the processor 206 in step 410. In the first instance, the first set of quality checks may involve determining whether the motion of the heartbeat sensor during the time period T1 for which the autocorrelation was computed in step 406 satisfies a certain motion-related criteria that indicates the amount of motion of the heartbeat sensor. If the criteria is not satisfied, i.e. there was too much motion of the heartbeat sensor during the time period T1 to have a high confidence on HR estimation from the PPG data acquired in that time, then the method 400 would proceed back to steps 402 and 404, as described above. Otherwise the method 400 would proceed to step 412. In such an example, the processor 206 would assess in step 410 the presence of motion that was evaluated in step 408. To that end, in some embodiments, the processor 206 could use the activity parameter determined in step 408 from the data samples of the second signal to evaluate the motion of the heartbeat sensor. For example, the processor 206 could determine whether the activity parameter is below a predefined threshold (or, more generally, satisfies a predefined criteria) that indicates that the heartbeat sensor was relatively still during the acquisition of the PPG signal over the time period T1.

Figure 6:
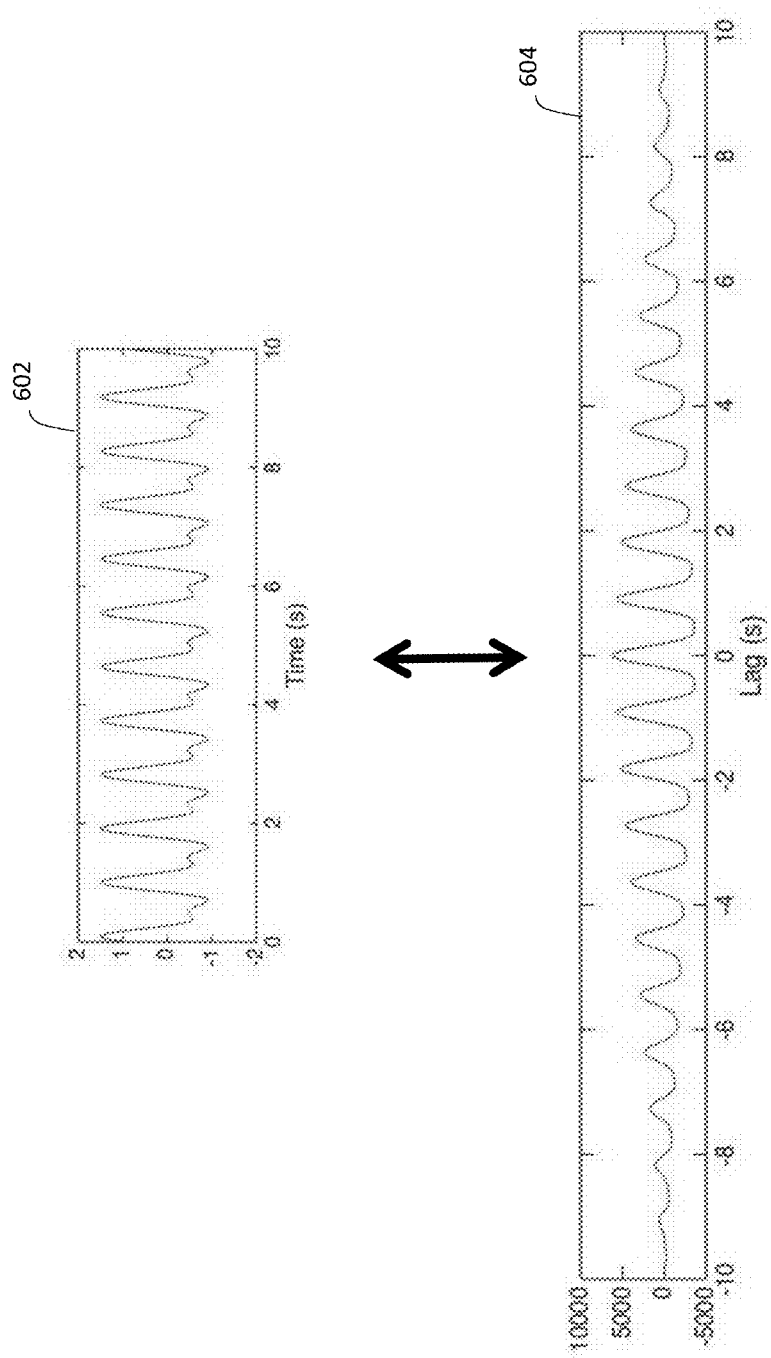
FIG. 6 illustrates an example of autocorrelation of a relatively clean sum-of-sinusoids signal with a strong fundamental frequency, according to some embodiments of the disclosure.

In other embodiments, the first set of confidence checks may include determination of whether the result of the autocorrelation (or SDF) computed in step 406 satisfied a certain set of one or more autocorrelation (or SDF) related criteria. In some embodiments, these checks may be based on expectations of how the autocorrelation (or SDF) of clean periodic signal should look like. One such check could be determining whether the autocorrelation function peaks are in decreasing order starting from the lag of zero to larger lags. A relatively ideal situation is illustrated in FIG. 6, where the top plot 602 illustrates a relatively clean (i.e. not noisy) sum-of-sinusoids signal which could be a PPG heartbeat signal, and the bottom plot 604 illustrates an autocorrelation of such a signal. As can be seen in the plot 604, the autocorrelation has a distinct characteristic largest peak at time lag of zero seconds, followed by a series of decreasing peaks as the time lag deviates further and further from zero.

In some embodiments, when computing and/or evaluating the results of autocorrelation, the processor 206 may be configured to only compute and/or evaluate autocorrelation with certain time lags that would correspond to reasonable expected heart rates. For example, the autocorrelation could be examined for lags from 0.25 seconds to 2 seconds, corresponding to, respectively 240 bpm and 30 bpm (60 seconds/minute divided by 0.25 seconds is equal to 240 beats per minute (bpm), while 60 seconds/minute divided by 2 seconds is equal to 30 bpm). Such limitation could advantageously reduce unnecessary computation/processing by the processor 206 since the heart rate of a living being would typically not be outside of these bounds. In various embodiments, the range of time lags to be evaluated could vary, dependent on a particular implementation and ease of design. For example, the right column of FIG. 7, described below, illustrates autocorrelation in a different range of time lags, corresponding to heart rates in the range of 40-240 bpm.

Figure 7:
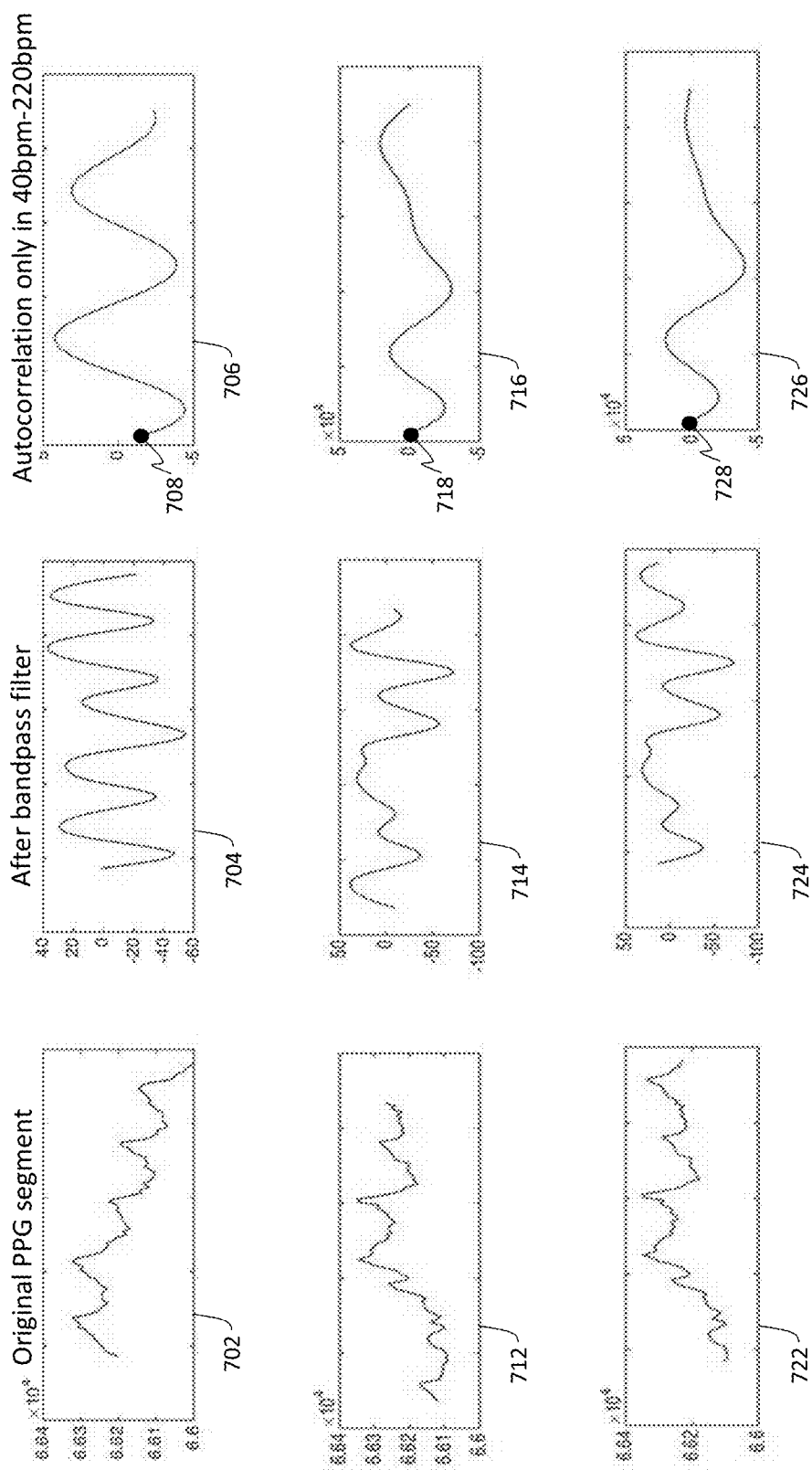
FIG. 7 illustrates three examples of autocorrelation of PPG signals with various degrees of noisiness, according to some embodiments of the disclosure.

While FIG. 6 illustrates an ideal situation, FIG. 7 shows three different scenarios of signals that may be acquired in real life—shown with plots 702, 712, and 722 illustrating examples of relatively noisy PPG signals. After a band-pass filter which may be applied to each of the acquired PPG signals 702, 712, and 722 in order to only evaluate frequencies which could potentially correspond to the heart rate, as described above, the PPG signals 702, 712, and 722 become as shown with plots 704, 714, and 724, respectively. An autocorrelation computed for such filtered PPG signals 704, 714, and 724 would then be as shown with plots 706, 716, and 726, respectively. It should be noted that the right column of FIG. 7 illustrates autocorrelation results only for certain time lags that correspond to expected heart rates, as described above, namely for time lags between 0.27 seconds (corresponding to 220 bpm heart rate) to 1.5 seconds (corresponding to 40 bpm heart rate).

The autocorrelation for the first scenario shown in FIG. 7 (i.e. the autocorrelation 706 for the scenario of the first row) looks as expected in that the peaks are in decreasing order, if considered from the smallest to the largest lag (i.e. the first peak from the left is the largest and the peak further to the right is smaller). If the processor 206 is configured to check this aspect of the autocorrelation computed in step 406 as a part of performing the first set of confidence checks in step 410, then the PPG signal 702 with such an autocorrelation would pass the confidence check.

On the other hand, the autocorrelation 716 of the second scenario shown in FIG. 7 (i.e. for the scenario of the second row shown in FIG. 7) would not pass the confidence check because the peak on the right side of the plot 716 is larger than the peak on the left side of the plot 716. Such an autocorrelation result is indicative of an irregular, i.e. noisy, PPG signal, in which case HR estimation on such data would not have the required sufficient level of confidence. Therefore, the processor 206 would conclude in step 410 that the first set of checks is not satisfied and proceed to consider further data samples of the PPG and accelerometer signals in steps 402 and 404.

In yet another example, the autocorrelation 726 of the third scenario shown in FIG. 7 (i.e. for the scenario of the third row shown in FIG. 7) may be considered to be somewhere in between the relatively clean example of the first row and the very noisy example of the second row. In the autocorrelation 726, the second peak is smaller than the first peak and the signal quality checker would have labeled this as reliable and a first heart rate estimate may have been computed. However, this example illustrates that a second and sometimes a third set of quality checks may be useful in order to reject estimates from such noisy data estimates that may pass the first set of quality checks.

Based on the foregoing description, a person of ordinary skill in the art would recognize that, in various embodiments of implementing step 410, the processor 206 may be configured with various further criteria of confidence checks based on the autocorrelation computed in step 406, all of which are within the scope of the present disclosure. For example, the processor 206 could be configured to evaluate whether a left-most edge value of the autocorrelation for the desired range of time lags is smaller than the first peak, as is usually empirically observed for an autocorrelation of a reasonably clean sum-of-sinusoids PPG signal. These edge values are indicated with dots 708, 718, and 728 for the three examples shown in FIG. 7. In FIG. 7 all of the edge values are shown to satisfy the autocorrelation criteria, but if such an edge value would be larger than the first peak, then even though the further local peaks could be in the decreasing order, it would be indicative of an unreliable PPG signal which should not pass the first set of quality checks in step 410. In yet another example, the autocorrelation-related criteria could include the consideration of autocorrelation peaks only those which satisfy a criterion indicative of the strength of the peak as compared to its neighboring peaks (e.g. having a prominence above a given threshold or being in a set of a predetermined number of peaks with the largest prominences).

In some embodiments, the processor 206 may be configured to perform, in step 410, both the motion-related confidence checks based on the results of the evaluation of the data samples of the second signal in step 408 and one or more of the autocorrelation- (or SDF-) related confidence checks based on the results of the autocorrelation (or SDF) computed for the data samples of the first signal in step 406.

Turning back to the step 412 shown in FIG. 4, the processor 206 may be configured to compute an HR estimate using any of the known algorithms for obtaining HR from an autocorrelation sequence. In some embodiments, the processor 206 may be configured to determine the first HR value based on the first peak of the autocorrelation that was computed in step 406. To that end, the processor 206 could be configured to e.g. fit a second order polynomial to the peak point and its immediate neighbors, and find the peak of that polynomial for better resolution of HR.

Steps 406, 408, 410, and 412 may be considered to implement step 302 of the more general method shown in FIG. 3, as indicated with a dashed box 302 surrounding these steps in FIG. 4. In some deployment scenarios, the processor 206 may continue only implementing the steps 402, 404, 406, 408, and 410 for some time if the data of the first and/or second signals is such that it may not be considered sufficiently reliable for computing the HR estimate based on the PPG data over the time period T1 in step 412. Once, however, the first set of confidence checks 410 is passed and the first HR estimate is computed, in step 412, from the autocorrelation obtained in step 406, the method may proceed to the second stage where the second and final HR estimates may be obtained. This is illustrated in FIG. 4 with an arrow from step 412 to a step shown within a dashed box 304.

In this second stage, the processor 206 may be configured to compute a DFT from the data samples of the first signal over a second time period, T2 (step 414), which would be greater than the first time period T1. In some embodiments, step 414 may include the processor 206 processing the data samples of the first signal over the second time period in any manner, other than DFT, that would allow determination, in step 418, of the second HR estimate from the results of such processing. For example, any of the known HR estimation techniques may be used in that step.

Figure 5:
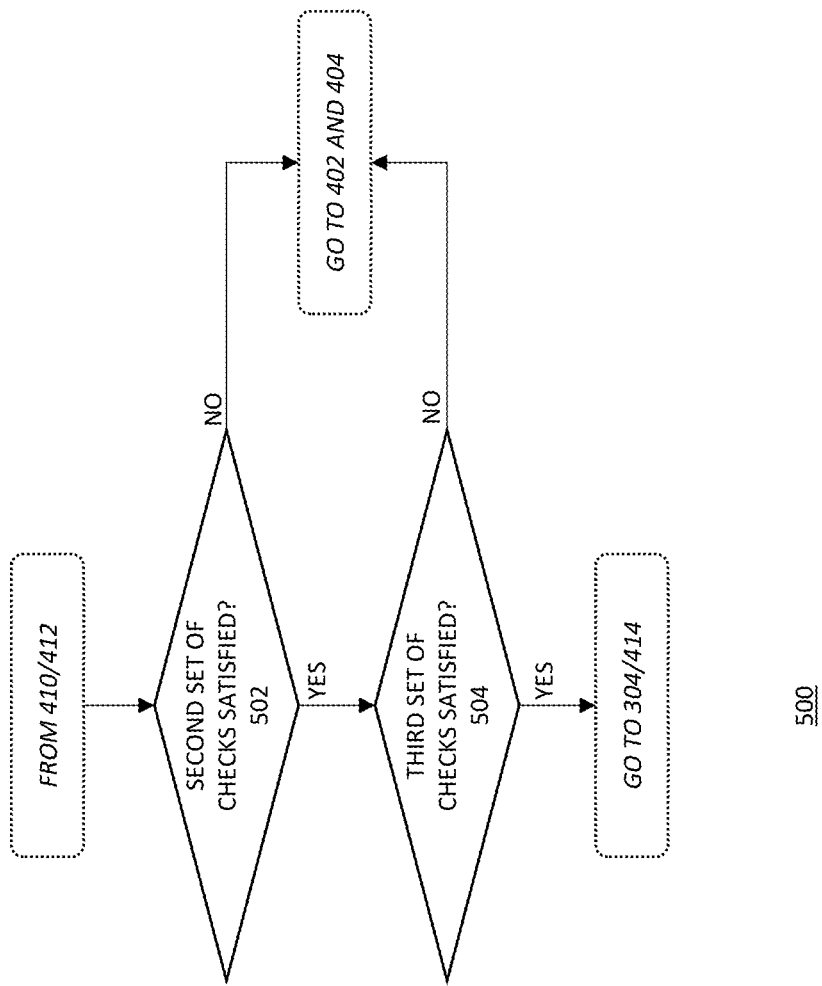
FIG. 5 illustrates additional confidence checks for a method for determining a heart rate from a PPG signal, according to some embodiments of the disclosure.

In some embodiments, the processor 206 may, optionally, be configured to only perform step 414 after it determines that some further sets of confidence checks are satisfied, as illustrated with an example shown in FIG. 5. Namely, FIG. 5 illustrates a method 500 of performing one or more additional confidence checks for a method for determining a heart rate from a PPG signal, such as e.g. the method 300 or 400, according to some embodiments of the disclosure.

As shown in FIG. 5, following step 412 or step 410 in which it was determined that the first set of confidence checks is satisfied, the method 400 may proceed with the method 500 where the processor 206 may be configured to perform a second set of confidence checks (step 502) and, optionally, also a third (and further) sets of confidence checks (step 504). As illustrated in FIG. 5, the processor 206 would then be configured to only proceed to the second stage processing of step 304 (e.g. to step 414 where the DFT for the data samples of the PPG signal is computed) if these further confidence checks are satisfied, indicating that the PPG signal is of sufficiently good quality to yield a high confidence HR estimation. Otherwise the processor 206 would go back to collecting more data samples of the first and second signals in steps 402 and 404.

The second set of confidence checks 502 could e.g. include evaluating the data samples of the PPG signal over the first time period T1 to determine whether an autocorrelation computed for these data samples in step 406 agrees with a heart rate estimate computed in step 412. In particular, the processor 206 could be configured to use the first HR estimate that it computed in step 412 to determine the number of local peaks that would be expected in an autocorrelation of the PPG data samples over the first time period T1, and then determine whether the determined expected number of peaks is, in fact, equal to the number of peaks present in the autocorrelation computed in step 406. This works as follows. Consider that in step 412 the processor 206 determined the heart rate to be 160 bpm. This means, that for an autocorrelation in a range of lags between 0.25 and 2 seconds one would expect 5 peaks computed as the number of heart beat periods that would fit in the 0.25-2 seconds range (the value of 5 peaks is arrived at as an int(2*(160/60), where int( ) implies the integer part of the computed number). The processor 206 would then access results of the autocorrelation computed in step 406 to determine whether the autocorrelation there has that number of peaks. In further embodiments, the processor 206 could be configured to determine whether a deviation in the number of peaks in the autocorrelation computed in step 406 from the number of expected autocorrelation peaks computed from the HR estimate of step 412 is within a predefined margin of error, e.g. not more than one peak difference.

If the second set of confidence checks 502 is not satisfied, then the processor 206 may be configured to go back to the start (i.e. steps 402 and 404). Otherwise it may proceed to the next set of confidence checks, shown as checks 504 in FIG. 5. The third set of confidence checks 504 could e.g. include the processor 206 determining whether the data samples of the PPG signal over a certain second time period T2 pass one or more checks of the first set of confidence checks (e.g. the first set of confidence checks as described above with reference to step 410 but now for the second time period T2). The DFT of step 414 could then only be computed upon determination that the data samples of the PPG signal over the time period T2 pass the confidence checks as well.

In some embodiments, the second time period T2 is preferably greater than and includes the first time period T1. Configuring the checks in this manner would allow accumulating a longer data segment that is reliable and long enough to obtain a more precise second HR estimate. In such embodiments, determining whether the PPG samples over the time period T2 satisfy the first set of confidence checks could include determining whether all past PPG sample chunks of duration T1 that are within time period T2 satisfied the confidence checks (which results could e.g. be stored in the memory 218). For example, consider that T1=4 seconds and T2=5 seconds and that the sampling rate for the PPG signal is 100 Hz (which means that there are 400 samples in a 4-second chunk of the PPG signal and 500 samples in a 5-second chunk of the PPG signal). The processor 206 may be configured to continuously determine whether the first set of checks is satisfied for each 4-second long period of PPG data, e.g. in a form of a sliding window, and storing indications of whether or not the first set of confidence checks were satisfied. Such an indication could e.g. be in a form of a flag which is set when first set of confidence checks is satisfied for a particular 4-seconds long chunk of PPG samples. Continuing with the example of T1=4 s and T2=5 s, this would mean that checking whether the PPG samples over the time period T2 satisfy the first set of confidence checks would mean checking whether the quality flags set for each of the 4-second windows indicate that all of the 4-second chunks satisfied the checks. Thus, about 101 flags in total could be checked: flag 1 corresponding to window 1 of PPG data samples from 1 to 400, flag 2 corresponding to window 2 of PPG data samples from 2 to 401, flag 3 corresponding to window 3 of PPG data samples from 3 to 402, and so on until flag 101 corresponding to window 101 of PPG data samples from 101 to 500. If all, or a predetermined number, of these were labeled as "good" data segments (i.e. PPG data samples of T1-long chunks that passed the first set of confidence checks), then the processor 206 may be configured to decide the PPG signal of last 5 seconds is good, and proceed to the second HR estimation of step 304. In other embodiments, T1 and T2 could be different, and the window could be shifted by a different number of data samples, e.g. by 2 or more samples. The latter would result in less autocorrelation functions being computed, although at the risk of missing some "bad" data samples in the PPG signal.

Thus, in general, the processor 206 could be configured to compute a series of autocorrelations of the data samples of the PPG signal within the second time period T2 (note that the autocorrelations are computed within the time period T2, not over the time period T2), each autocorrelation of the series being computed over a period that is equal to the first time period T1. In such embodiments, the confidence checks of step 504 could include determining whether the outcome of the each autocorrelation of the series of autocorrelations (i.e. over each autocorrelation over time period T1, sliding with a sliding window) satisfies one or more checks of the first set of confidence checks as described with reference to step 410.

Figure 8:
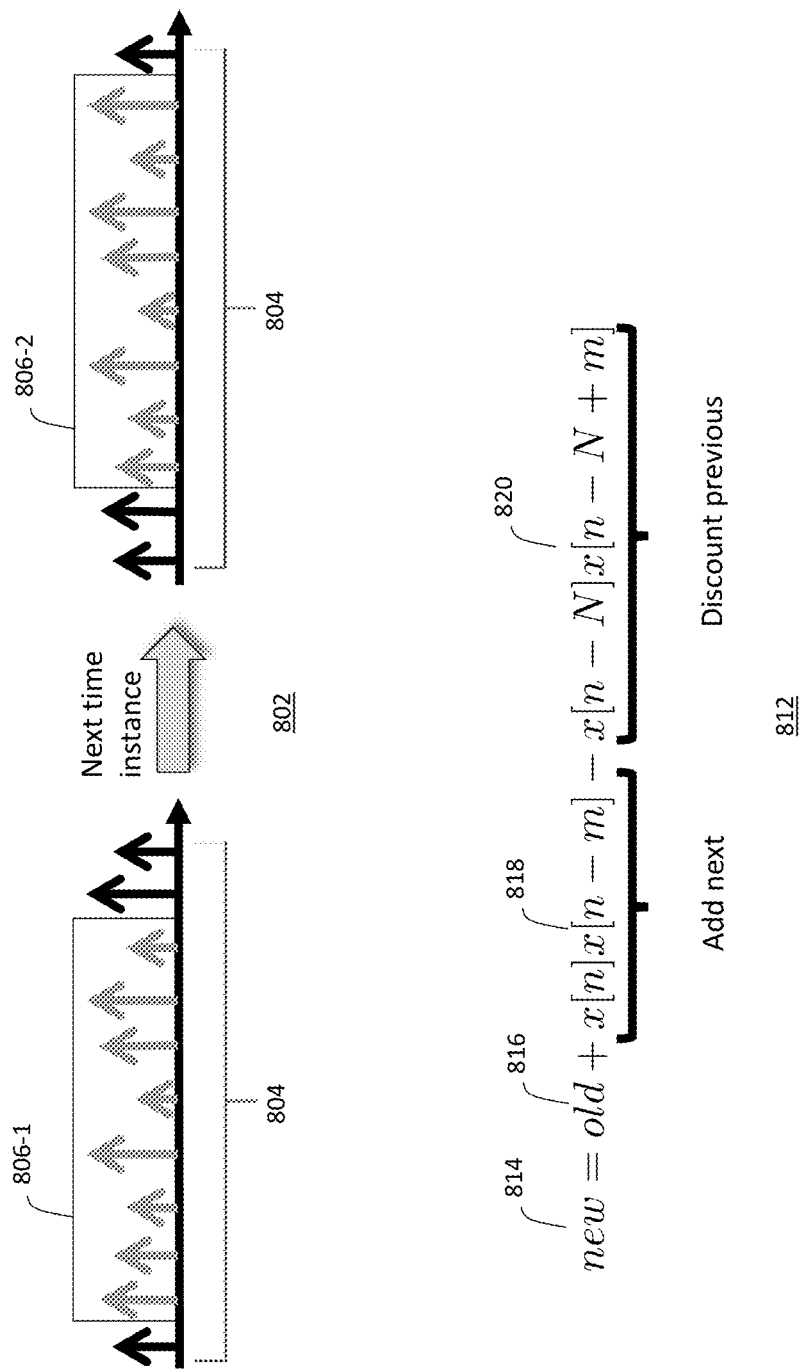
FIG. 8 illustrates an example of a computation of streaming autocorrelation with a shifting window, according to some embodiments of the disclosure.

In some embodiments, the autocorrelations of the consecutive shifting windows may be performed in a streaming manner. In such embodiments, the processor 206 may be configured to compute the autocorrelation of the data samples of the PPG signal over the second time period T2 by performing iterations of adding a contribution due to a new data sample (that just entered the window) to an autocorrelation of a previous iteration and subtracting a contribution due to a former data sample (that just left the window) for each new data sample of the PPG data samples between the last data sample of the T1-worth of data samples of the PPG signal and the last data sample of the T2-worth of data samples of the PPG signal. Such streaming processing is illustrated in FIG. 8. The top illustration 802 shows a stream of PPG data samples 804, where the vertical arrows illustrate relative magnitudes of the data points of the PPG signal. The illustration 802 provides an example with 11 data samples of PPG signal. The left side of the illustration shows a first instance of a time window T1, shown as a window 806-1, over which the autocorrelation is computed. In particular, the example of the illustration 802 shows that, out of the 11 PPG data samples 1 through 11 shown in 802, the time window 806-1 includes PPG data samples 2 through 9 (thus the T1 worth of PPG data samples in this example includes 8 data samples). Once an autocorrelation over the time window 806-1 is computed, the window 806-1 shifts, e.g. by 1 data sample as shown in FIG. 8, arriving at a window 806-2. The window 806-2 also include 8 data samples of the PPG signal, but the second data sample that was present in the window 806-1 now has left the window and the $10^{th}$ data sample that was just outside of the window 806-1 now has entered the window. An autocorrelation for the window 806-2 may then be computed as shown with a formula 812 in FIG. 8 where an autocorrelation 814 for the "new" window 806-2 is computed by taking the "old" autocorrelation result 816 for the window 806-1, adding a contribution 818 to autocorrelation due to the next data sample that entered the window 806 and subtracting the contribution 820 to autocorrelation due to the data sample that left the window 806. In 818 and 820, the integer n denotes the time index of the last data sample in the window, N is the window size (8 in this example) and the integer m denotes the particular lag for which the autocorrelation is currently being computed. The integer m may be varied for all the lags that are of interest, in particular for all the values that corresponds to a meaningful heart rate for a living being.

Of course, FIG. 8 is purely illustrative, in that, in various embodiments, other time windows and other numbers of data samples within the window (which would depend e.g. on the sampling rate) could be used. Even in the example of T1=4 seconds and sampling rate of 100 Hz, the window of duration T1 would include many more samples than what is shown in the illustration 802 (namely, the window would include 400 samples, as described above).

Configuring the processor 206 to compute the autocorrelation in the streaming way as described above may be more efficient than computing the autocorrelation block-wise (i.e. by completely re-computing the autocorrelation for each new window) for a number of reasons. First, it eliminates the need to unnecessarily repeating some computations as the window is shifted. Second, in case the processor may start with computing the autocorrelation in an initial phase where the autocorrelation window is expanding, which is described in greater detail in the next paragraph, it avoids making a large computation for all T1-worth of PPG data samples at once, and distributes the computation to earlier samples as well.

In some embodiments, the processor 206 may be configured to start performing steps similar to those shown in box 302 of FIG. 4 before it has acquired the T1 period worth of PPG data samples. This may be the case when the PPG measurements are just beginning and may be done in order to speed up HR estimation. In such embodiments, e.g. if the processor 206 has less than 400 data samples (for the example of 100 Hz sampling rate and T1 being equal to 4 seconds), then it may start performing steps 406-408 for the lesser number of samples and the autocorrelation window, instead of shifting as shown in FIG. 8 for the case when T1-worth of data samples has already been acquired, is expanding, to cover more and more PPG data samples, until the window reaches the window size for T1 period of data samples.

The time periods of 4 seconds for T1 and 5 seconds for T2 are purely exemplary and may differ in different embodiments. Also, in some embodiments, the processor 206 may be configured to start performing steps 406-412 at e.g. 250 samples (i.e. for a time period less than T1). And as soon as a certain larger number of data samples is acquired, e.g. 350, the processor 206 may be configured to check for the flags of past data segments to assess whether it is a good time to compute a second HR estimate. The combination of smaller time periods (e.g. at 100 Hz sampling rate, this example corresponds to a [2.5 sec, 3.5 sec] combination) may potentially provide a faster response than a longer time period combination.

In some embodiments, the shorter time windows may be used early on, when system just started acquiring the data samples, and the processor 206 may be configured to switch to the longer combination of time periods T1 and T2 once enough data samples are received. Continuing with the example provided above, once the processor 206 acquired the 2.5 seconds worth of data, it may be configured to not start shifting the autocorrelation window yet, but continue to expand it until 4 seconds, and only after that the processor may start shifting if it still has not gotten to a point where it has good enough data to make an HR estimate (i.e. some confidence checks failed, forcing the processor to go back to steps 402 and 404 and acquire and analyze more data samples).

Turning back to block 304 of FIG. 4, in step 414, after all of the confidence checks have been satisfied, the processor 206 may be configured to compute the DFT for the data samples of the PPG signal over the second time period T2. Any of the methods for computing DFT may be employed and are within the scope of the present disclosure. Since such methods are known in the art, they are not described here in greater detail.

Optionally, although not shown in FIG. 4, prior to computing the DFT, the processor 206 may be configured to decimate the T2-period worth of PPG data to a lower sampling rate (e.g. from 100 Hz to 10 Hz) and then compute the DFT on the decimated data. Such decimation may, first, advantageously allow to "zoom" into a smaller frequency axis, e.g. a frequency axis between −5 Hz to +5 Hz, and therefore obtain a better frequency resolution if the same number of DFT samples are used. Second, such decimation may reduce the computational burden of DFT computing if a DFT is chosen to be computed for fewer samples instead, for the same frequency resolution.

Once the DFT over the time period T2 has been computed, the processor 206 may be configured to directly proceed to step 418 where it computes a second HR estimate based on the computed DFT. For example, similar to the way the first HR estimate may be computed from autocorrelation, in step 418 the processor 206 may be configured to fit a second order polynomial to the peak point of the DFT and its immediate neighbors, and find the peak of that polynomial to obtain the second HR estimate. In other embodiments, any of suitable known methods for determining a heart rate from a DFT may be employed and are within the scope of the present disclosure. Since such methods are known in the art, they are not described here in greater detail.

The processor 206 may then be configured to compare the first and second HR estimates computed in steps 412 and 418 respectively to determine whether they reasonably agree with one another (step 420) and, if so, determine the final HR estimate, which may be provided as the output device 216, based on the outcome of the comparison (step 422). If the processor 206 determines in step 420 that the first and second HR estimates are not within a reasonable agreement, it may go back to steps 402 and 404 to receive and analyze more data samples.

In various embodiments, different comparison criteria may be employed by the processor 206, all of which being within the scope of the present disclosure. For example, the processor 206 may be configured to determine whether the first HR estimate from step 412, or some parameter indicative thereof, and the second HR estimate from step 418, or some parameter indicative thereof, are within a predefined number of bpm from one another, e.g. within 5 bpm from one another. The processor 206 may then be configured to declare the final HR e.g. as being equal to the second HR estimate (i.e. the DFT estimate), or as being equal to the first HR estimate (i.e. the autocorrelation-based estimate), or as being equal to an estimate computed based on the first and second estimates (e.g. being equal to a weighted average of the first and the second estimates).

If T2 is larger than T1, then there will almost always be more than one HR estimate for each block of T1 that satisfied the first set of confidence checks (i.e. more than one of "first HR estimates" computed in steps 412). In such cases, comparison performed by the processor 206 in step 420 may include comparing the second HR estimate to e.g. a mean of these multiple first estimates (i.e. the mean of multiple first estimates would be the "estimate indicative of the first estimate").

In some optional embodiments, once the processor 206 computed the DFT in step 414, it may be configured to determine whether certain DFT-related checks are satisfied (step 416), prior to proceeding with step 418. This provides yet another level of confidence checks that would allow establishing the final HR estimate with high confidence. If, in step 416, the processor 206 determines that the DFT-related checks are not satisfied, it may go back to steps 402 and 404 to receive and analyze more data samples.

One DFT-based check that may be performed in step 416 includes determining whether an absolute value of the DFT has a local peak in a feasible range of heart rates. This would provide an implicit signal quality check in addition to those that were applied in steps 410 and optional steps 502 and/or 504. In some embodiments, this may involve checking whether there is a peak in the absolute value of the DFT, which may be computed by any suitable FFT algorithm, e.g. inside the band of interest, e.g. 0.5 Hz to 4 Hz. At this point, the processor 206 may be configured to determine that the peak is not exactly at the edges of this band of interest. If there is no clear and prominent peak, then the processor 206 may go back to steps 402 and 404. If there is such a peak, then the processor may further be configured to determine that a certain multiple of this peak should not be lower than the other peaks in the band of interest (e.g. 0.5 Hz to 4 Hz) interval. Alternatively or additionally, the processor 206 may be configured to determine whether there are any DFT values below the lower limit of the band of interest, e.g. below 0.5 Hz, that are larger than a certain multiple of this DFT peak for it to qualify for an HR estimate. DFT values above the higher limit of the band of interest, e.g. above 4 Hz, are less important to compare since they are usually small if the initial optional filtering with a low-pass or band-pass filter was performed.

By computing a final HR based on at least two HR estimates obtained by different HR estimation methods and by performing a sequence of signal quality/confidence checks, the processor 206 may advantageously provide the final HR of step 422 with reasonably high confidence.

In some embodiments of the present disclosure, instead of performing autocorrelation, the processor 206 may be configured to use SDF instead, or both SDF and AF, or other functions including but not limited to the ratio of AF and SDF or ratio of differences and sums of AF and SDF, that are indicative of repeating patterns due to heartbeats in the PPG signal.

In some embodiments, the PPG signal may be decimated to lower sampling rates, e.g. to 25 Hz, prior to computing the autocorrelation or SDF in step 406. Doing so may reduce computational burden and may make the algorithm more robust.

In some embodiments where quality flags are set as described above, the processor 206 may still conclude that confidence checks for the data samples over a period T2 are still satisfied even though some of the flags indicate that some data samples did not satisfy all of the quality checks. In various embodiments, indicators other than flags described herein may be used to keep track of whether a set of data samples has passed one or more sets of confidence checks. Such information may e.g. be contained in any kind of database/table.

In some embodiments, the processor 206 may use "prominence" of the peaks in the autocorrelation or the normalized SDF function. Prominence is a measure of how important a peak is when compared to the neighboring peaks, and may especially be useful if the signal is noisy because it allows disregarding some large peaks because they are relatively buried in other peaks that are very close to it (and thus exhibiting lower prominence). The processor 206 may, e.g., be configured to only account for peaks with prominence larger than a threshold, or the peaks with the largest three prominences, etc.

In some embodiments, the processor 206 may allow for some of the samples to have "activity" larger than the predefined threshold used in step 408. This may make the method more robust in that the T1-period worth of data samples are not discarded due to only a limited amount of high motion samples.

In some embodiments, if the DFT computed in step 414 satisfies the quality checks of step 414, but the second HR estimate did not agree with the first HR estimate of step 412, then the processor 206 may be configured to store that DFT value for a predefined number of cycles to avoid computing it again since the HR is not likely to change that fast. Doing so may provide the autocorrelation another chance to agree with the HR estimate from the DFT. This situation may happen with a few new data segments, e.g. the discrepancy was 5.1 bpm and waiting a little will allow it go below 5 bpm.

In some embodiments, instead of decimating the PPG signal to e.g. 10 Hz (e.g. before performing step 414), the processor 206 may be configured to send each incoming data sample to a one of the 10 separate data buffers. When the processor then wants to compute the DFT of the last e.g. 5 seconds, it will access the correct buffer to read the data samples. Since there are 10 data buffers in this example, each one of them will be holding a decimated version of the data by 10. These buffers come at extra cost of memory, but may allow avoiding the decimation operation.

Various features and examples described above as being in one of the embodiments, may be combined, in any order and in any number, in other embodiments. Some of the variations are described above. Some further possible examples of variations are described below, providing a non-exhaustive list of possible variations of the embodiments within the scope of the present disclosure.

While examples described herein are based on using motion data from three accelerometer channels, the improved methods 300, 400, and/or 500 for HR estimation may also be implemented in an analogous manner by using only one or two of the accelerometer channels, or by using some combination of two or more accelerometer channels.

While many examples described herein are described in relation to a frequency representative of a heartbeat, it is envisioned that the improved methods 300, 400, and/or 500 can be applicable in other scenarios for estimating other types of frequencies from a first signal. Furthermore, while the examples herein are described with one or more input signals provided by one or more optical sensors, it is envisioned that the method can be used to filter the input signals generated by other types of sensors, including but not limited to: optical sensor, audio sensor, capacitive sensor, magnetic sensor, chemical sensor, humidity sensor, moisture sensor, pressure sensor, and biosensor.

Furthermore, more than one optical sensor may be used and data obtained therefrom may be processed according to the improved methods 300, 400, and/or 500 described above. For example, the wavelengths used for measuring input signals for PPG can span wavelengths from blue to infrared. In classic deployment scenarios, LEDs of two colors—often 660 nm and 940 nm—may be used for measuring blood oxygen saturation. These devices are in large volume production and are readily available. In yet another deployment scenario, a simple single-color LED—say at 940 nm, may be used to measure heart rate by measuring the periodic variation in a return signal. In some cases, a green LED is used to pick up variation in absorption caused by blood flow on the wrist. Different wavelengths of light reflects differently from skin (due to the pigmentation and wrinkles, and other features of the skin) and different optical sensors tend to behave differently in the presence of motion when sensing light reflected from skin. Based on this insight, it is possible to infer information about presence of motion and/or the quality of a PPG signal. It is also possible to improve the data samples to be processed according to the improved methods 300, 400, and/or 500 based on the insight. Multiple light sources having different wavelengths can be used (e.g., a red LED and a green LED). For instance, by sensing these light sources and examining differences between the input signals of optical sensors for detecting light having respective wavelengths, or different portions of a spectrum of an input signal from a wideband optical sensor, it is possible to infer whether certain data samples of the PPG signal is likely to have been affected by motion or some other artifact.

SELECTED EXAMPLES

Some Examples in accordance with various embodiments of the present disclosure are now described.

Example 1 provides a computer-implemented method for determining a heart rate from a heartbeat signal present in a first signal (PPG signal) generated by a heartbeat sensor (optical sensor). The method may include computing (406) an autocorrelation of data samples of the first signal over a first time period (T1); processing (408) a second signal to evaluate motion of the heartbeat sensor during the first time period, the second signal indicative of a motion of the heartbeat sensor with respect to one or more directions; determining (410) whether the data samples of the first signal over the first time period pass a first set of confidence/quality checks, the first set of confidence checks including at least determining whether the motion of the heartbeat sensor during the first time period satisfies a motion-related criteria; upon determination that the data samples of the first signal over the first time period pass the first set of confidence checks, computing (412) a first estimate of the heart rate from the autocorrelation of the data samples of the first signal over the first time period; computing (414) a Discrete Fourier Transform (DFT) for data samples of the first signal over a second time period (T2); computing (418) a second estimate of the heart rate from the DFT; and determining (422) the heart rate based on the first estimate and the second estimate.

Example 2 provides the method according to Example 1, where the second time period is greater than and includes the first time period.

Example 3 provides the method according to Examples 1 or 2, further including determining (504) whether the data samples of the first signal over the second time period pass the first set of confidence checks, where the DFT is computed upon determination that the data samples of the first signal over the second time period pass the first set of confidence checks.

Example 4 provides the method according to Example 3, further including computing a series of autocorrelations of the data samples of the first signal within the second time period, each autocorrelation of the series of autocorrelations computed over a period that is equal to the first time period, where the first set of confidence checks further includes determining whether the outcome of the each autocorrelation satisfies an autocorrelation-related criteria.

Example 5 provides the method according to Example 4, where computing the autocorrelation of the data samples of the first signal over the second time period includes performing iterations of adding a contribution due to a new data sample to an autocorrelation of a previous iteration and subtracting a contribution due to a former data sample for each new data sample of data samples between a last data sample of the data samples of the first signal over the first time period and a last data sample of the data samples of the first signal over the second time period.

Example 6 provides the method according to Examples 1 or 2, further including determining (502) whether the data samples of the first signal over the first time period pass a second set of confidence checks, where the DFT is computed upon determination that the data samples of the first signal over the first time period pass the second set of confidence checks.

Example 7 provides the method according to Example 6, further including determining an expected number of local peaks in the autocorrelation of the data samples of the first signal over the first time period based on the first heart rate estimate, where the second set of confidence checks includes determining whether the determined expected number of local peaks is equal to a number of local peaks present in the autocorrelation of the data samples of the first signal over the first time period.

Example 8 provides the method according to any one of the preceding Examples, further including computing a series of autocorrelations of the data samples of the first signal within the second time period, each autocorrelation of the series of autocorrelations computed over a period that is equal to the first time period, where the first set of confidence checks further includes determining whether the outcome of the each autocorrelation satisfies autocorrelation-related criteria or a predetermined number of autocorrelations of the series of autocorrelations satisfy autocorrelation-related criteria.

Example 9 provides the method according to Example 8, determining whether the each autocorrelation of the data samples of the first signal over the first time period satisfies the autocorrelation-related criteria is carried out only for a portion of the each autocorrelation for which an autocorrelation lag is between 0.25 seconds and 2 seconds. The 0.25 seconds lag corresponds to a heart rate of 240 bpm (240 bpm=1 beat/0.25 seconds*60 seconds/minute), while the 2 seconds lag corresponds to a heart rate of (30 bpm=1 beat/2 seconds*60 seconds/minute). Limiting evaluation of the autocorrelation outcomes to lags between 0.25 and 2 seconds effectively means only evaluating the results where a reasonable heart rate could be (i.e. between 30 and 240 bpm).

Example 10 provides the method according to Example 9, where the autocorrelation-related criteria include determining whether an autocorrelation peak that occurs first within the portion of the each autocorrelation is larger than any other autocorrelation value within the portion of the each autocorrelation.

Example 11 provides the method according to Examples 9 or 10, where the autocorrelation-related criteria includes determining whether autocorrelation peaks occur within the portion of the each autocorrelation in order of decreasing magnitude values (i.e. the peak that occurs first is greater in magnitude than the peak that occurs second, the peak that occurs second is greater than the peak that occurs third, and so on).

In yet a further Example of the method according to Examples 9, 10 or 11, the autocorrelation-related criteria could include the consideration of autocorrelation peaks only those which satisfy a criterion indicative of the strength of the peak as compared to its neighboring peaks (e.g. having a prominence above a given threshold of being in a set of a predetermined number of peaks with the largest prominences).

Example 12 provides the method according to any one of the preceding Examples, further including using the data samples of the second signal to determine a parameter (referred to herein as "activity") indicative of the motion of the heartbeat sensor, where the motion-related criteria includes determining whether the parameter is below a predefined threshold that indicates that the heartbeat sensor was relatively still during the acquisition of the first signal over the time period of interest.

Example 13 provides the method according to any one of the preceding Examples, further including determining (416) whether an absolute value of the DFT has a local peak in a feasible range of heart rates, where the second estimate of the heart rate is computed upon determination that the absolute value of the DFT has the local peak in the feasible range of heart rates.

Example 14 provides the method according to any one of the preceding Examples, where determining the heart rate based on the first estimate and the second estimate includes determining whether the first estimate and the second estimate, or values indicative thereof, are within a predefined number of beats per minute (bpm) from one another, and, upon determining that the first estimate and the second estimate are within the predefined number of bpm from one another, determining the heart rate as equal to one of the first estimate, the second estimate, or an estimate computed based on the first estimate and the second estimate (e.g. a weighted average of the first and the second estimates).

Example 15 provides the method according to any one of the preceding Examples, further including decimating the data samples of the first signal over the second time period prior to computing the DFT and computing the DFT on the decimated data samples.

Example 16 provides the method according to any one of the preceding Examples, further including processing the first signal and/or the second signal with a pre-processing filter to substantially attenuate signal content outside of a reasonable frequency band of interest corresponding to a range of reasonable heart rates.

Example 17 provides the method according to Example 16, where the pre-processing filter is a low-pass filter or a band-pass filter; and the reasonable frequency band of interest includes frequencies between 0.5 Hertz and 4 Hertz.

Example 18 provides the method according to any one of the preceding Examples, further including applying a filter or mask to or removing a portion of the first signal indicative of a saturation condition of the heartbeat sensor.

Example 19 provides a computer-implemented method for determining a heart rate from a heartbeat signal present in a first signal (PPG signal) generated by a heartbeat sensor (optical sensor). The method may include computing (406) an squared difference function (SDF) on data samples of the first signal over a first time period (T1); processing (408) a second signal to evaluate motion of the heartbeat sensor during the first time period, the second signal indicative of a motion of the heartbeat sensor with respect to one or more directions; determining (410) whether the data samples of the first signal over the first time period pass a first set of confidence/quality checks, the first set of confidence checks including at least determining whether the motion of the heartbeat sensor during the first time period satisfies a motion-related criteria; upon determination that the data samples of the first signal over the first time period pass the first set of confidence checks, computing (412) a first estimate of the heart rate from the SDF of the data samples of the first signal over the first time period; computing (414) a Discrete Fourier Transform (DFT) for data samples of the first signal over a second time period (T2); computing (418) a second estimate of the heart rate from the DFT; and determining (422) the heart rate based on the first estimate and the second estimate.

Example 20 provides a computer-implemented method for determining a heart rate from a heartbeat signal present in a first signal (PPG signal) generated by a heartbeat sensor (optical sensor). The method may include computing (406) both an autocorrelation function (AF) and an squared difference function (SDF) on data samples of the first signal over a first time period (T1); computing a combination function representative of the computed autocorrelation function and the computed squared difference function; processing (408) a second signal to evaluate motion of the heartbeat sensor during the first time period, the second signal indicative of a motion of the heartbeat sensor with respect to one or more directions; determining (410) whether the data samples of the first signal over the first time period pass a first set of confidence/quality checks, the first set of confidence checks including at least determining whether the motion of the heartbeat sensor during the first time period satisfies a motion-related criteria; upon determination that the data samples of the first signal over the first time period pass the first set of confidence checks, computing (412) a first estimate of the heart rate from the combination function of the data samples of the first signal over the first time period; computing (414) a Discrete Fourier Transform (DFT) for data samples of the first signal over a second time period (T2); computing (418) a second estimate of the heart rate from the DFT; and determining (422) the heart rate based on the first estimate and the second estimate.

Example 21 provides the method according to Example 20, wherein the combination function is computed as 1−SDF/(SDF+2*AF).

Further Examples provide the method according to any one of Examples 2-18 but using SDF instead of AF as provided in Example 19 or using a combination of SDF and AF as provided in Example 20. In other words, further Examples provide methods according to either Example 19 or Examples 20 or 21, further combined with features of any one of Examples 2-18.

Example 22 provides another computer-implemented method for determining a heart rate from a heartbeat signal present in a first signal generated by a heartbeat sensor. The method of Example 22 may include processing a second signal to evaluate motion of the heartbeat sensor during a first time period, the second signal indicative of a motion of the heartbeat sensor with respect to one or more directions; and determining whether data samples of the first signal over the first time period pass a first set of confidence checks, the first set of confidence checks comprising at least determining whether the motion of the heartbeat sensor during the first time period satisfies a motion-related criteria. Upon determination that the data samples of the first signal over the first time period pass the first set of confidence checks, the method of Example 22 may include computing a first estimate of the heart rate from the data samples of the first signal over the first time period using a first heart rate estimation algorithm, computing a second estimate of the heart rate from the data samples of the first signal over the first time period using a second heart rate estimation algorithm, and determining the heart rate based on the first estimate and the second estimate.

Example 23 provides an apparatus for determining a heart rate from a heartbeat signal present in a first signal generated by a heartbeat sensor, the apparatus comprising at least one memory configured to store computer executable instructions, and at least one processor coupled to the at least one memory and configured, when executing the instructions, to perform a method according to any one of the preceding Examples.

Example 24 provides a non-transitory computer readable storage medium storing software code portions configured, when executed on a processor, to determine a heart rate from a heartbeat signal present in a first signal generated by a heartbeat sensor by carrying out a method according to any one of the preceding Examples.

Example 25 provides an apparatus comprising means for performing a method according to any one of the preceding Examples.

Further variations and implementations

It is envisioned that a heart rate measuring apparatus as described herein can be provided in many areas including medical equipment, security monitoring, patient monitoring, healthcare equipment, medical equipment, automotive equipment, aerospace equipment, consumer electronics, and sports equipment, etc.

In some cases, the heart rate measuring apparatus can be used in professional medical equipment in a healthcare setting such as doctor's offices, emergency rooms, hospitals, etc. In some cases, the heart rate measuring apparatus can be used in less formal settings, such as schools, gyms, homes, offices, outdoors, under water, etc. The heart rate measuring apparatus can be provided in a consumer healthcare product.

The heart rate measuring apparatus or parts thereof can take many different forms. Examples include watches, rings, wristbands, chest straps, headbands, headphones, ear buds, clamps, clips, clothing, bags, shoes, glasses, googles, hats, suits, necklace, attachments/patches/strips/pads which can adhere to a living being, accessories, portable devices, and so on. In particular, wearables technology (or referred often as "wearables", i.e., electronics which are intended to be worn by humans or other living beings) can greatly leverage the benefits of the heart rate measuring apparatus disclosed herein due to the wearables' portability and the heart rate monitoring technique's robustness against motion artifacts. Even in the presence of noise, the wearable can effectively measure/track a heart rate. Besides wearables, portable or mobile devices such as mobile phones and tablets can also include a processor having the tracking functions, an analog front end, a light source and a light sensor (or an extension (wired or wireless) having the light source and light sensor) to provide a heart rate measuring apparatus. Users can advantageously use a ubiquitous mobile phone to make a heart rate measurement. Furthermore, it is envisioned that the heart rate measuring apparatus can be used in wired or wireless accessories such as cuffs, clips, straps, bands, probes, etc., to sense physiological parameters of a living being. These accessories can be connected to a machine configured to provide the processor and the analog front end. The analog front end could be provided in the accessory or in the machine.

Besides measuring a heart rate, the heart rate measuring apparatus can be provided to sense or measure other physiological parameters such as oxygen saturation (SpO2), blood pressure, respiratory rate, activity or movement, etc. Besides humans, the heart rate measuring apparatus can be provided to measuring frequencies present in signals sensing other living beings such as animals, insects, plants, fungi, etc.

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure. For instance, instead of processing the signals in the digital domain, it is possible to provide equivalent electronics that can process the signals in the analog domain.

In one example embodiment, any number of electrical circuits may be used to implement the HR estimation techniques as described herein, and, in particular, to implement elements shown in the FIGUREs. Such electrical circuits may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities. In some cases, application specific hardware can be provided with or in the processor to carry out those functionalities.

In another example embodiment, the electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the improved HR estimation functionalities may be implemented in one or more silicon cores in Application Specific Integrated Circuits (ASICs), Field Programmable Gate Arrays (FPGAs), and other semiconductor chips.

Note that the activities discussed above with reference to the FIGURES are applicable to any integrated circuits that involve signal processing, particularly those that can execute specialized software programs, or algorithms, some of which may be associated with processing digitized real-time data to measure or track a heart rate. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include pulmonary monitors, heart rate monitors, pacemakers, etc. Other applications can involve automotive technologies for safety systems (e.g., stability control systems, driver assistance systems, braking systems, infotainment and interior applications of any kind). Furthermore, powertrain systems (for example, in hybrid and electric vehicles) can use high-precision data conversion products in battery monitoring, control systems, reporting controls, maintenance activities, etc. It is envisioned that these applications can also utilize the disclosed HR estimation techniques. In yet other example scenarios, the teachings of the present disclosure can be applicable in the industrial markets that include process control systems aiming to measure HR to help drive productivity, energy efficiency, and reliability.

Note that with the numerous examples provided herein, interaction may be described in terms of two, three, four, or more parts. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the features of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, parts, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to improved HR estimation techniques described herein, illustrate only some of the possible tracking functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Although the claims are presented in single dependency format in the style used before the USPTO, it should be understood that any claim can depend on and be combined with any preceding claim of the same type unless that is clearly technically infeasible.

What is claimed is:

1. A system for determining a heart rate from a heartbeat signal present in a first signal generated by a heartbeat sensor, the system comprising:
    means for computing an autocorrelation of data samples of the first signal over a first time period;
    means for processing a second signal to evaluate motion of the heartbeat sensor during the first time period, the second signal indicative of a motion of the heartbeat sensor with respect to one or more directions;
    means for determining whether the data samples of the first signal over the first time period pass a set of confidence checks, the set of confidence checks comprising at least
        determining whether the motion of the heartbeat sensor during the first time period satisfies a motion-related criteria;
    means for computing a first estimate of the heart rate from the autocorrelation of the data samples of the first signal over the first time period upon determination that the data samples of the first signal over the first time period pass the set of confidence checks;
    means for computing a Discrete Fourier Transform (DFT) for data samples of the first signal over a second time period;
    means for computing a second estimate of the heart rate from the DFT; and
    means for determining the heart rate based on a comparison of the first estimate and the second estimate.

2. The system according to claim 1, wherein the second time period is greater than and includes the first time period.

3. The system according to claim 2, further comprising means for determining whether the data samples of the first signal over the second time period pass the set of confidence checks, wherein the DFT is computed upon determination that the data samples of the first signal over the second time period pass the set of confidence checks.

4. The system according to claim 3, further comprising means for computing a series of autocorrelations of the data samples of the first signal within the second time period, each autocorrelation computed over a period that is equal to the first time period, wherein the set of confidence checks further comprises determining whether the outcome of the each autocorrelation satisfies an autocorrelation-related criteria.

5. The system according to claim 4, wherein computing the autocorrelation of the data samples of the first signal over the second time period comprises performing iterations of adding a contribution due to a new data sample to an autocorrelation of a previous iteration and subtracting a contribution due to a former data sample for each new data sample of data samples between a last data sample of the data samples of the first signal over the first time period and a last data sample of the data samples of the first signal over the second time period.

6. The system according to claim 1, wherein the set of confidence checks is a first set of confidence checks, and the system further includes means for determining whether the data samples of the first signal over the first time period pass a second set of confidence checks, wherein the DFT is computed upon determination that the data samples of the first signal over the first time period pass the second set of confidence checks.

7. The system according to claim 6, further comprising means for determining an expected number of local peaks in the autocorrelation of the data samples of the first signal over the first time period based on the first heart rate estimate,
wherein the second set of confidence checks comprises determining whether the expected number of local peaks is equal to a number of local peaks present in the autocorrelation of the data samples of the first signal over the first time period.

8. The system according to claim 1, further comprising means for computing a series of autocorrelations of the data samples of the first signal within the second time period, each autocorrelation computed over a period that is equal to the first time period,
wherein the set of confidence checks further comprises determining whether the outcome of the each autocorrelation satisfies autocorrelation-related criteria or a predetermined number of autocorrelations satisfy autocorrelation-related criteria.

9. The system according to claim 8, wherein determining whether the outcome of the each autocorrelation satisfies the autocorrelation-related criteria is carried out only for a portion of the each autocorrelation for which an autocorrelation lag is between 0.25 seconds and 2 seconds.

10. The system according to claim 9, wherein the autocorrelation-related criteria comprise determining whether an autocorrelation peak that occurs first within the portion of the each autocorrelation is larger than any other autocorrelation value within the portion of the each autocorrelation.

11. The system according to claim 9, wherein the autocorrelation-related criteria comprises determining whether autocorrelation peaks occur within the portion of the each autocorrelation in order of decreasing values.

12. The system according to claim 1, further comprising:
means for using the data samples of the second signal to determine a parameter indicative of the motion of the heartbeat sensor,
wherein the motion-related criteria comprises determining whether the parameter is below a predefined threshold.

13. The system according to claim 1, further comprising means for determining that an absolute value of the DFT has a local peak in a feasible range of heart rates.

14. The system according to claim 1, wherein determining the heart rate based on the comparison of the first estimate and the second estimate comprises:
determining whether the first estimate and the second estimate are within a predefined number of beats per minute (bpm) from one another, and
upon determining that the first estimate and the second estimate are within the predefined number of bpm from one another, determining the heart rate as equal to one of the first estimate, the second estimate, or an estimate computed based on the first estimate and the second estimate.

15. The system according to claim 1, further comprising means for decimating the data samples of the first signal over the second time period prior to computing the DFT and computing the DFT on the decimated data samples.

16. The system according to claim 1, further comprising:
means for processing the first signal and/or the second signal with a pre-processing filter to substantially attenuate signal content outside of a reasonable frequency band of interest corresponding to a range of reasonable heart rates.

17. A system for determining a heart rate from a heartbeat signal present in a signal generated by a heartbeat sensor, the system comprising:
means for computing an autocorrelation of data samples of the signal over a first time period;
means for determining whether the data samples of the signal over the first time period satisfy a motion-related criteria;
means for computing, when the data samples of the signal over the first time period satisfy the motion-related criteria, a first estimate of the heart rate based on the autocorrelation;
means for computing a Fourier Transform (FT) for data samples of the signal over a second time period;
means for computing a second estimate of the heart rate based on the FT; and
means for determining the heart rate based on a comparison of the first estimate and the second estimate.

18. The system according to claim 17, wherein the means for determining whether the data samples of the signal over the first time period satisfy the motion-related criteria include means for determining whether the data samples of the signal over the first time period satisfy the motion-related criteria based on a second signal indicative of a motion of the heartbeat sensor with respect to one or more directions.

19. A system for determining a heart rate from a heartbeat signal present in a first signal generated by a heartbeat sensor, the system comprising:
means for computing an autocorrelation of data samples of the signal over a first time period;
means for determining whether the data samples of the signal over the first time period satisfy a motion-related criteria;
means for computing, when the data samples of the signal over the first time period satisfy the motion-related criteria, a first estimate of the heart rate based on the autocorrelation;
means for computing a Fourier Transform (FT) for data samples of the signal over a second time period, wherein the second time period includes the first time period;
means for computing a second estimate of the heart rate based on the FT; and
means for determining the heart rate based the first estimate and the second estimate.

20. The system according to claim 19, wherein determining the heart rate based on the first estimate and the second estimate includes:
- determining whether the first estimate and the second estimate are within a predefined number of beats per minute (bpm) from one another, and
- upon determining that the first estimate and the second estimate are within the predefined number of bpm from one another, determining the heart rate as equal to one of the first estimate, the second estimate, or an estimate computed based on the first estimate and the second estimate.

* * * * *